(12) United States Patent
Stevens et al.

(10) Patent No.: US 9,700,200 B2
(45) Date of Patent: Jul. 11, 2017

(54) DETECTING VISUAL IMPAIRMENT THROUGH NORMAL USE OF A MOBILE DEVICE

(71) Applicant: INTERNATIONAL BUSINESS MACHINES CORPORATION, Armonk, NY (US)

(72) Inventors: Mark B. Stevens, Austin, TX (US); John D. Wilson, Houston, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 146 days.

(21) Appl. No.: 14/571,790

(22) Filed: Dec. 16, 2014

(65) Prior Publication Data
US 2016/0166204 A1   Jun. 16, 2016

(51) Int. Cl.
*A61B 5/00* (2006.01)
*A61B 3/00* (2006.01)
*A61B 3/113* (2006.01)

(52) U.S. Cl.
CPC .......... *A61B 3/0041* (2013.01); *A61B 3/0025* (2013.01); *A61B 3/113* (2013.01)

(58) Field of Classification Search
CPC .. A61B 3/00; A61B 3/02; A61B 3/024; A61B 3/028; A61B 3/032; A61B 3/06; A61B 3/08; A61B 3/09; A61B 3/113; A61B 3/0041; A61B 3/0025
See application file for complete search history.

(56) References Cited

U.S. PATENT DOCUMENTS

| | | | | |
|---|---|---|---|---|
| 8,827,451 B2 * | 9/2014 | Cabeza Guillen | ..... | A61B 3/085 351/201 |
| 8,894,209 B2 * | 11/2014 | Berry | ....................... | A61B 3/18 351/223 |
| 9,033,508 B2 * | 5/2015 | Bartlett | .................. | A61B 3/032 351/210 |

(Continued)

FOREIGN PATENT DOCUMENTS

WO   2013059331 A1   4/2013

OTHER PUBLICATIONS

"Netra: Refractive Tests on a Mobile Phone", MIT.edu, Pamplona et al, 2010, found on the world wide web at: http://web.media.mit.edu/~pamplona/NETRA/.

(Continued)

*Primary Examiner* — Max n Hindenburg
(74) *Attorney, Agent, or Firm* — Paul S. Drake

(57) ABSTRACT

A method, system or computer usable program product for detecting visual interaction factors indicative of visual impairment through normal use of a mobile device including monitoring and recording in memory visual interaction of a user with content presented by the mobile device during normal use of the mobile device in accordance with predetermined parameters; establishing a baseline pattern of visual interaction factors in accordance with the predetermined parameters; utilizing a processor to compare the visual interaction of the user with the baseline factors to determine a set of differences; and responsive to the set of differences exceeding a predetermined threshold, providing a notification of visual impairment.

20 Claims, 7 Drawing Sheets

(56) References Cited

U.S. PATENT DOCUMENTS

| | | | | |
|---|---|---|---|---|
| 9,039,182 B2* | 5/2015 | Huang | ............ | G06K 9/46 |
| | | | | 351/239 |
| 9,111,144 B2* | 8/2015 | Fogg | ............ | G06K 9/00617 |
| 9,155,461 B2* | 10/2015 | Bartlett | | |
| 9,226,870 B2* | 1/2016 | Wu | ............ | A61B 3/02 |
| 9,282,886 B2* | 3/2016 | Scherlen | ............ | A61B 3/02 |
| 9,329,680 B2* | 5/2016 | Yoon | ............ | G06F 3/011 |
| 9,357,917 B2* | 6/2016 | Agarwal | ............ | A61B 3/113 |

OTHER PUBLICATIONS

"Human Visual System Based Rate Scalable Video Coding", IP.com, No. IPCOM000014938D, published Jan. 29, 2002, found on the world wide web at: http://priorart.ip.com/IPCOM/000014938.

"Mobile Device Resource Conservation During Geo-Location Operations", IP.com, No. IPCOM000231493D, published Oct. 2, 2013, found on the world wide web at: http://priorart.ip.com/IPCOM/000231493.

* cited by examiner

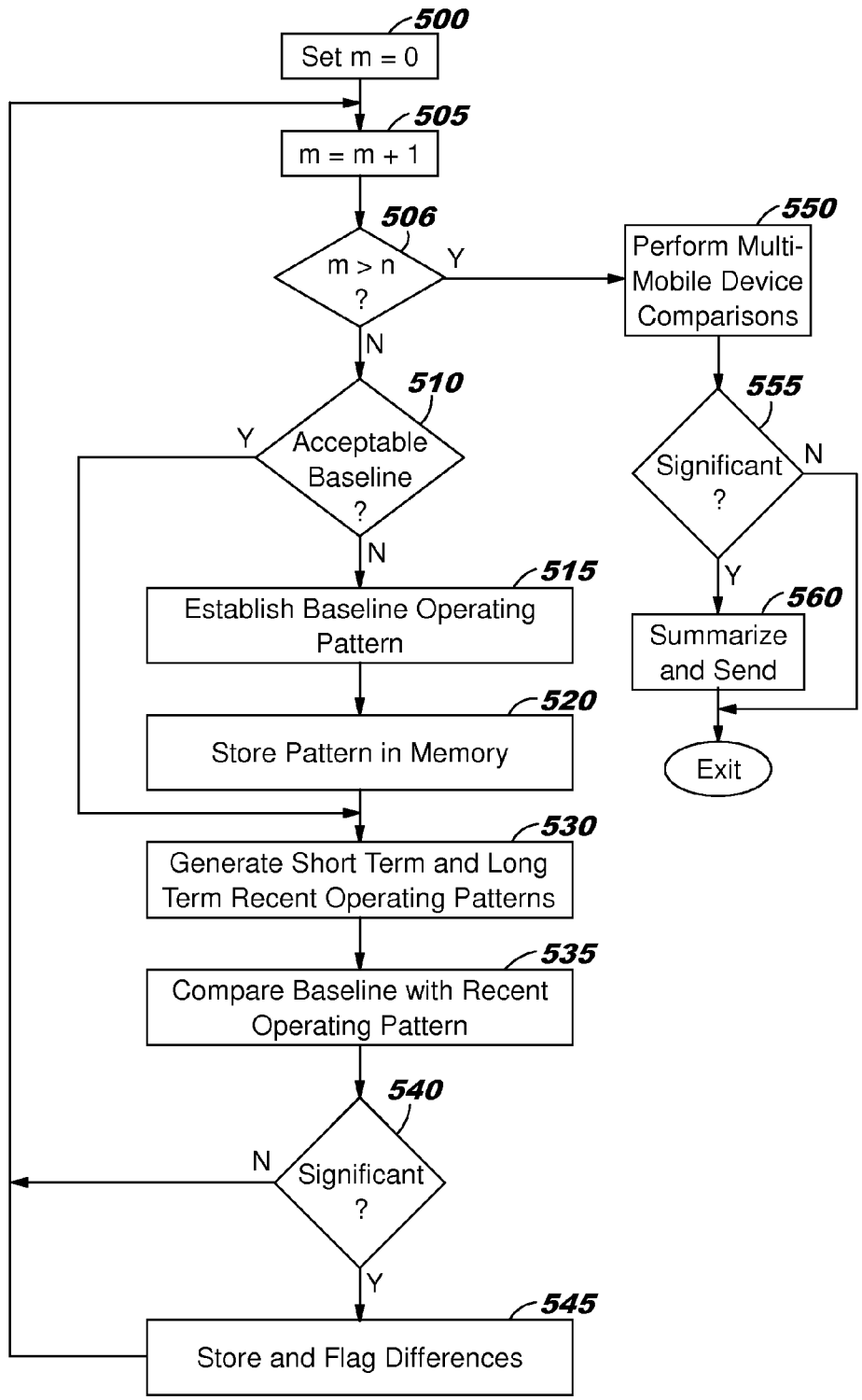

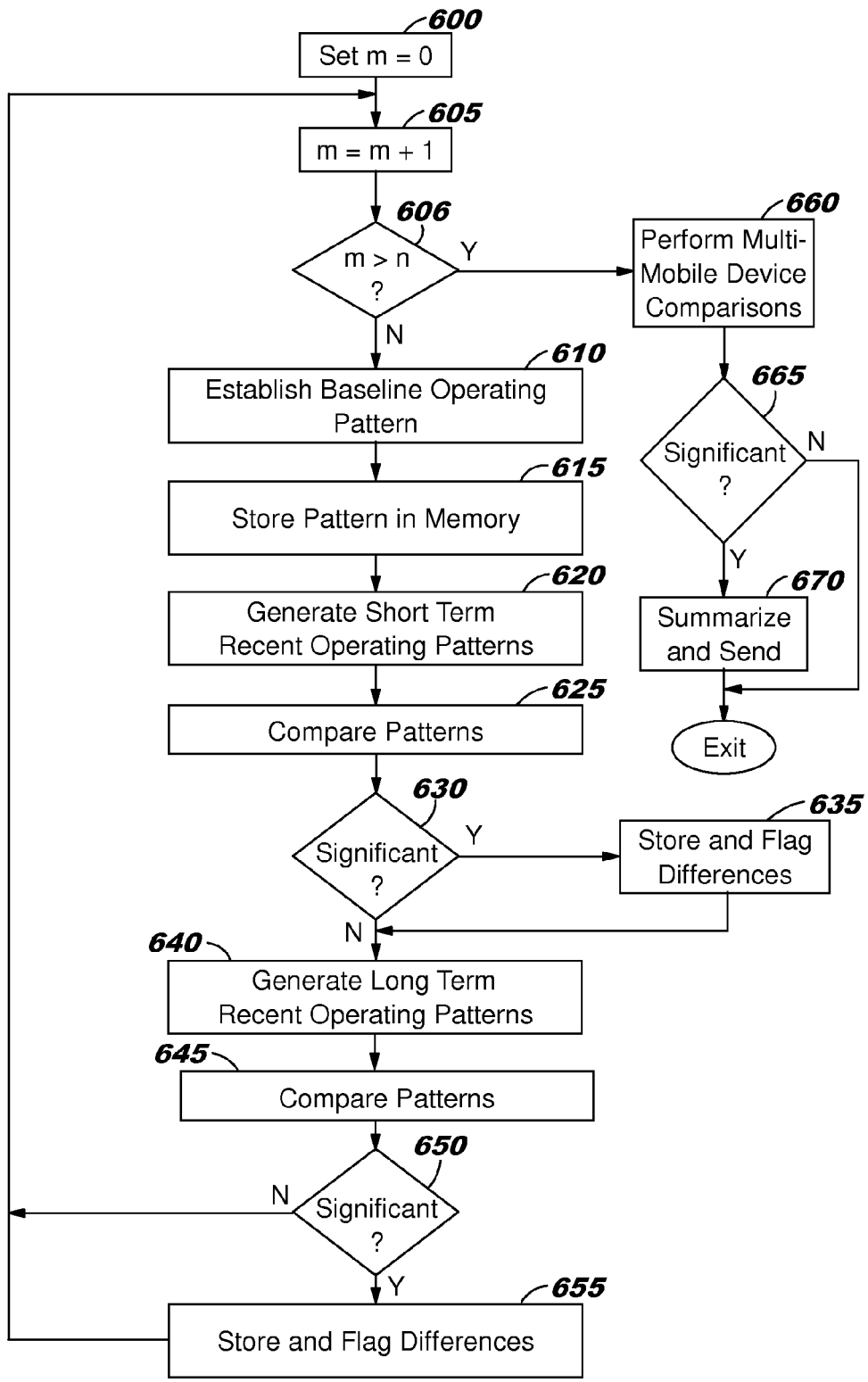

| Mobile Device 705 | Mobile Device Activity 710 | Parameter Ranges 715 | Sensor Capabilities 720 | Possible Events 725 | Threshold 730 |
|---|---|---|---|---|---|
| 1 | Email | 12 Pica, No Zoom, 50cm | Image, Display, Camera | Change Font, Zoom Image, Decrease Distance | 95% |

| USERID 755 | Time 760 | Mobile Device 765 | Activity Requested 770 | Parameters 775 | Sensor Results 780 | Events Detected 785 |
|---|---|---|---|---|---|---|
| John | 10pm 7/1/14 | 1 | Email | Font, Zoom, Distance | none | none |

DETECTING VISUAL IMPAIRMENT THROUGH NORMAL USE OF A MOBILE DEVICE

BACKGROUND

1. Technical Field

The present invention relates generally to detecting visual impairment, and in particular, to a computer implemented method for detecting visual impairment through normal use of a mobile device.

2. Description of Related Art

Visual impairment may have a variety of causes such as age related macular degeneration, Stargardt disease, retinoschisis, and cataracts. Many of these eye diseases are progressive with gradual visual degradation and some can affect people of all ages. With early detection, many of these diseases can be treated, thereby limiting visual impairment. For example, zinc supplements are associated with slowing the advance of macular degeneration. However, if the visual impairment is not detected early, then treatment may be limited and damage may be irreversible. As a result, early detection of visual impairment allows for intervention that could change the outcome or provide relief and assistance before substantial permanent visual damage has occurred.

Testing for indications of eye disease can be problematic with patients of all ages. Patients will often improve or alter their behavior in response to their being observed (e.g., the Hawthorne effect). This is a problem well known in the medical field and is one reason double blind tests may be utilized in medical experiments, including the use of placebos. For example, elderly patients are known to ask their caregiver the current date before visiting a physician, knowing that question will be asked by the physician. Also, children in schools are known to memorize eye charts to score well on eye exams.

SUMMARY

The illustrative embodiments provide a method, system, and computer usable program product for detecting visual interaction factors indicative of visual impairment through normal use of a mobile device including monitoring and recording in memory visual interaction of a user with content presented by the mobile device during normal use of the mobile device in accordance with predetermined parameters; establishing a baseline pattern of visual interaction factors in accordance with the predetermined parameters; utilizing a processor to compare the visual interaction of the user with the baseline factors to determine a set of differences; and responsive to the set of differences exceeding a predetermined threshold, providing a notification of visual impairment.

BRIEF DESCRIPTION OF THE SEVERAL VIEWS OF THE DRAWINGS

The novel features believed characteristic of the invention are set forth in the appended claims. The invention itself, further objectives and advantages thereof, as well as a preferred mode of use, will best be understood by reference to the following detailed description of illustrative embodiments when read in conjunction with the accompanying drawings, wherein:

FIG. 5 is a flow diagram of analyzing visual interaction with the mobile device for operating patterns indicating visual impairment in accordance with a first embodiment;

FIG. 6 is a flow diagram of analyzing visual interaction with the mobile device for operating patterns indicating visual impairment in accordance with a second embodiment; and FIGS. 7A-7B are block diagrams of data structures utilized for storing visual interaction with the mobile device for statistical analysis in which various embodiments may be implemented.

DETAILED DESCRIPTION

Processes and devices may be implemented and utilized for detecting visual impairment through normal use of a mobile device. These processes and apparatuses may be implemented and utilized as will be explained with reference to the various embodiments below.

Figure 1:
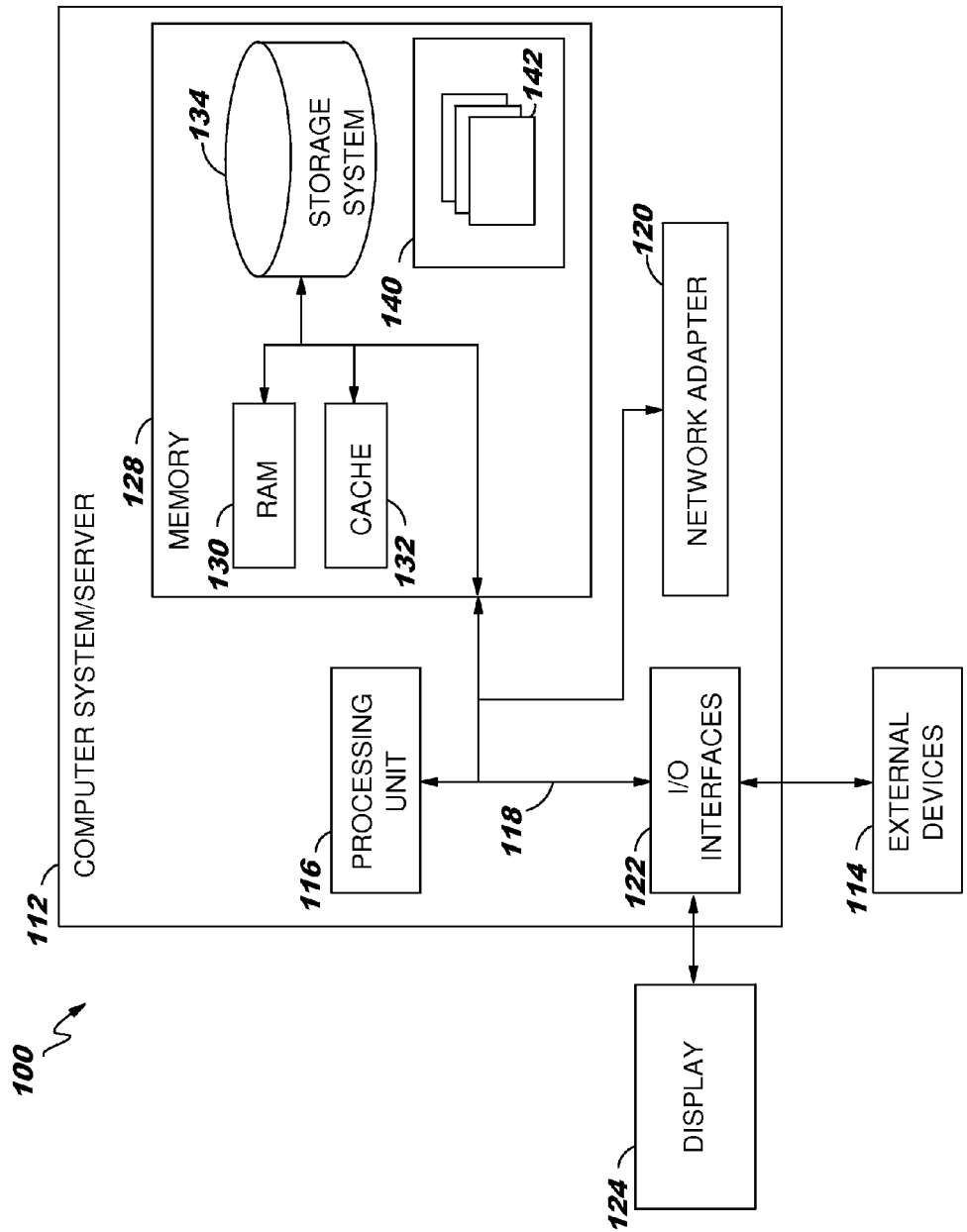
FIG. 1 is a block diagram of an illustrative data processing system in which various embodiments of the present disclosure may be implemented.

FIG. 1 is a block diagram of an illustrative data processing system in which various embodiments of the present disclosure may be implemented. Data processing system 100 is one example of a suitable data processing system and is not intended to suggest any limitation as to the scope of use or functionality of the embodiments described herein. Regardless, data processing system 100 is capable of being implemented and/or performing any of the functionality set forth herein such as detecting visual impairment through normal use of a mobile device.

In data processing system 100 there is a computer system/server 112, which is operational with numerous other general purpose or special purpose computing system environments, peripherals, or configurations. Examples of well-known computing systems, environments, and/or configurations that may be suitable for use with computer system/server 112 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 112 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 112 may be practiced in distributed computing environments where tasks are performed by remote processing devices that are linked through a communications network. In a distributed computing environment, program modules may be located in both local and remote computer system storage media including memory storage devices.

As shown in FIG. 1, computer system/server 112 in data processing system 100 is shown in the form of a general-purpose computing device. The components of computer system/server 112 may include, but are not limited to, one or more processors or processing units 116, a system memory 128, and a bus 118 that couples various system components including system memory 128 to processor 116.

Bus 118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 112 typically includes a variety of non-transitory computer system usable media. Such media may be any available media that is accessible by computer system/server 112, and it includes both volatile and non-volatile media, removable and non-removable media.

System memory 128 can include non-transitory computer system readable media in the form of volatile memory, such as random access memory (RAM) 130 and/or cache memory 132. Computer system/server 112 may further include other non-transitory removable/non-removable, volatile/non-volatile computer system storage media. By way of example, storage system 134 can be provided for reading from and writing to a non-removable, non-volatile magnetic media (not shown and typically called a "hard drive"). Although not shown, a USB interface for reading from and writing to a removable, non-volatile magnetic chip (e.g., a "flash drive"), and an optical disk drive for reading from or writing to a removable, non-volatile optical disk such as a CD-ROM, DVD-ROM or other optical media can be provided. In such instances, each can be connected to bus 118 by one or more data media interfaces. Memory 128 may include at least one program product having a set (e.g., at least one) of program modules that are configured to carry out the functions of the embodiments. Memory 128 may also include data that will be processed by a program product.

Program/utility 140, having a set (at least one) of program modules 142, may be stored in memory 128 by way of example, and not limitation, as well as an operating system, one or more application programs, other program modules, and program data. Each of the operating system, one or more application programs, other program modules, and program data or some combination thereof, may include an implementation of a networking environment. Program modules 142 generally carry out the functions and/or methodologies of the embodiments. For example, a program module may be software for detecting visual impairment through normal use of a mobile device.

Computer system/server 112 may also communicate with one or more external devices 114 such as a keyboard, a pointing device, a display 124, etc.; one or more devices that enable a user to interact with computer system/server 112; and/or any devices (e.g., network card, modem, etc.) that enable computer system/server 112 to communicate with one or more other computing devices. Such communication can occur via I/O interfaces 122 through wired connections or wireless connections. Still yet, computer system/server 112 can communicate with one or more networks such as a local area network (LAN), a general wide area network (WAN), and/or a public network (e.g., the Internet) via network adapter 120. As depicted, network adapter 120 communicates with the other components of computer system/server 112 via bus 118. It should be understood that although not shown, other hardware and/or software components could be used in conjunction with computer system/server 112. Examples, include, but are not limited to: microcode, device drivers, tape drives, RAID systems, redundant processing units, data archival storage systems, external disk drive arrays, etc.

Figure 2:
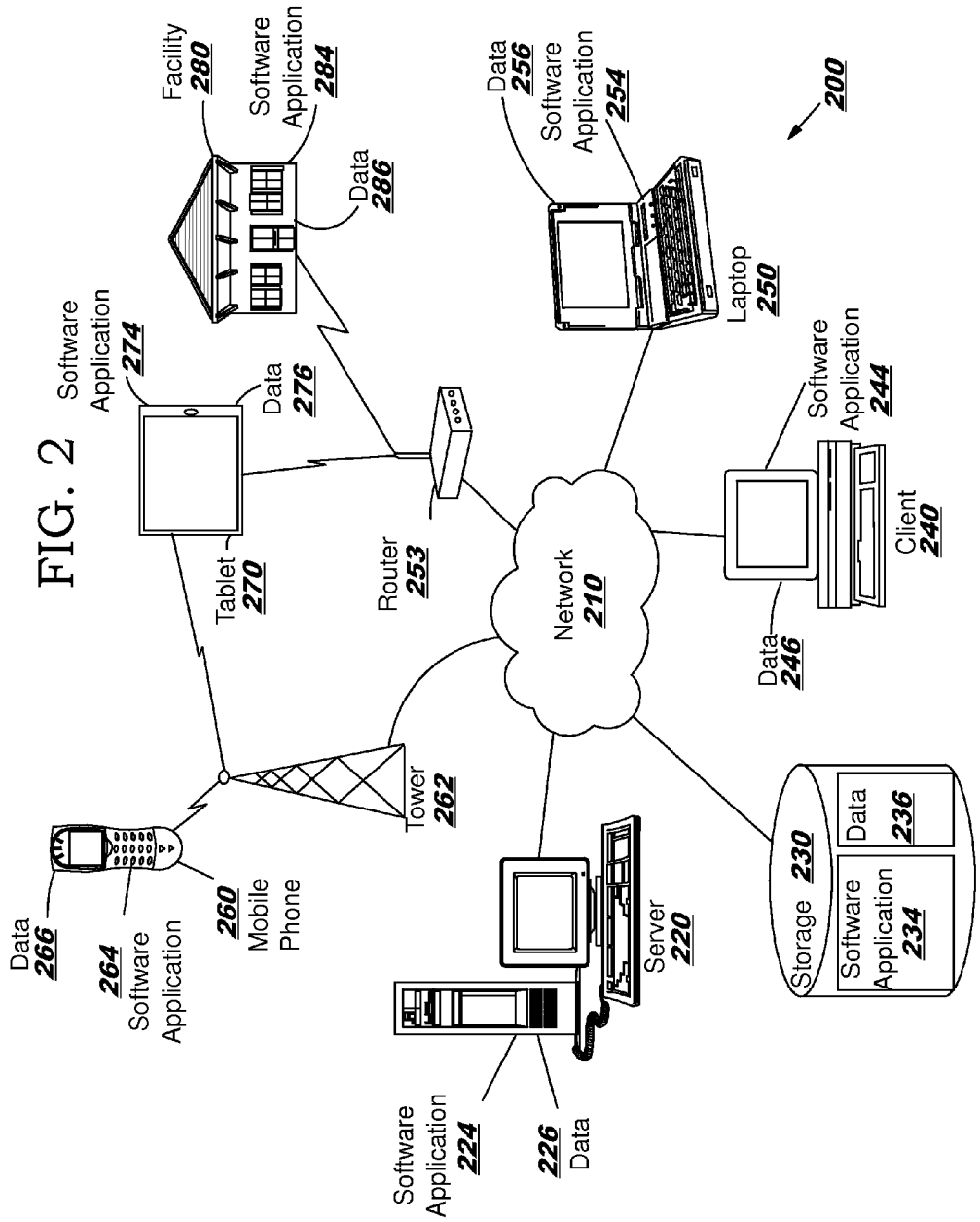
FIG. 2 is a block diagram of an illustrative network of data processing systems in which various embodiments of the present disclosure may be implemented.

FIG. 2 is a block diagram of an illustrative network of data processing systems in which various embodiments of the present disclosure may be implemented. Data processing environment 200 is a network of data processing systems such as described above with reference to FIG. 1. Software applications such as for detecting visual impairment through normal use of a mobile device may execute on any computer or other type of data processing system in data processing environment 200. Data processing environment 200 includes network 210. Network 210 is the medium used to provide simplex, half duplex and/or full duplex communications links between various devices and computers connected together within data processing environment 200. Network 210 may include connections such as wire, wireless communication links, or fiber optic cables.

Server 220 and client 240 are coupled to network 210 along with storage unit 230. In addition, laptop 250, tablet 270 and facility 280 (such as a home or business) are coupled to network 210 including wirelessly such as through a network router 253. A mobile phone 260 and tablet 270 may be coupled to network 210 through a mobile phone tower 262. Data processing systems, such as server 220, client 240, laptop 250, mobile phone 260, tablet 270 and facility 280 contain data and have software applications including software tools executing thereon. Other types of data processing systems such as personal digital assistants (PDAs), smartphones and netbooks may be coupled to network 210. These data processing systems include mobile devices such as PDAs, smartphones, tablets, laptops, netbooks, etc.

Server 220 may include software application 224 and data 226 for detecting visual impairment through normal use of a mobile device or other software applications and data in accordance with embodiments described herein. Storage 230 may contain software application 234 and a content source such as data 236 for detecting visual impairment through normal use of a mobile device. Other software and content may be stored on storage 230 for sharing among various computer or other data processing devices. Client 240 may include software application 244 and data 246. Mobile devices such as laptop 250, mobile phone 260, and tablet 270 may also include software applications 254, 264 and 274 as well as data 256, 266 and 276 for detecting visual impairment through normal use of those mobile device. Facility 280 may include software applications 284 and data 286. Other types of data processing systems coupled to network 210 may also include software applications. Software applications could include a web browser, email, or other software application for detecting visual impairment through normal use of a mobile device.

Server 220, storage unit 230, client 240, laptop 250, mobile phone 260, tablet 270 and facility 280 and other data processing devices may couple to network 210 using wired connections, wireless communication protocols, or other suitable data connectivity. Client 240 may be, for example, a personal computer or a network computer.

In the depicted example, server 220 may provide data, such as boot files, operating system images, and applications to client 240 and laptop 250. Server 220 may be a single computer system or a set of multiple computer systems working together to provide services in a client server environment. Client 240 and laptop 250 may be clients to server 220 in this example. Client 240, laptop 250, mobile phone 260, tablet 270 and facility 280 or some combination thereof, may include their own data, boot files, operating system images, and applications. Data processing environment 200 may include additional servers, clients, and other devices that are not shown.

In the depicted example, data processing environment 200 may be the Internet. Network 210 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 200 also may be implemented as a number of different types of networks, such as for example, an intranet, a local area network (LAN), or a wide area network (WAN). FIG. 2 is intended as an example, and not as an architectural limitation for the different illustrative embodiments.

Among other uses, data processing environment 200 may be used for implementing a client server environment in which the embodiments may be implemented. A client server environment enables software applications and data to be distributed across a network such that an application functions by using the interactivity between a client data processing system and a server data processing system. Data processing environment 200 may also employ a service oriented architecture where interoperable software components distributed across a network may be packaged together as coherent business applications.

Figure 3:
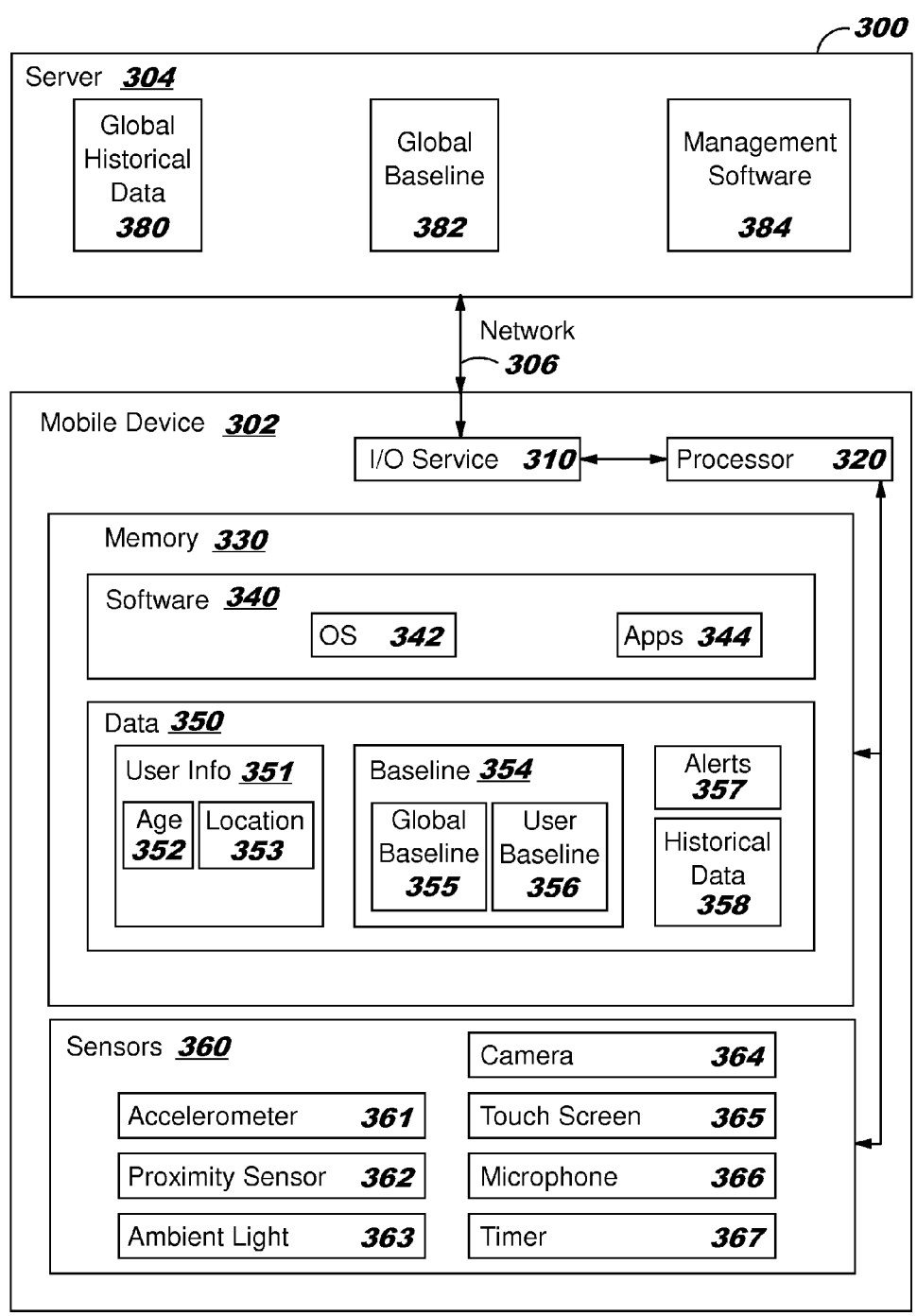
FIG. 3 is a block diagram of a mobile device in which various embodiments may be implemented.

FIG. 3 is a block diagram of a mobile device system in which various embodiments may be implemented. Mobile device system 300 includes a mobile device 302 which may be in communication with server(s) 304. Mobile device 302 is a small computing device, typically handheld, such as a mobile phone, smartphone, PDA, netbook, tablet, laptop, or other type of mobile device such as a smartwatch, head-mounted display, portable media player, etc. Mobile device 302 can be coupled with a server or servers 304, such as a cloud service, across a network 306. Network 306 may be the internet, a wide area network, a local area network, or other type of network which can be coupled to mobile device 302 and server(s) 304 wirelessly or wired.

Mobile device 302 includes input/output device(s) 310, processor 320, memory 330, and sensors 360. Input/output devices 310 are utilized for communications between mobile device 302 and server(s) 304 across network 306 and can include one or more types of modems or other communication devices for establishing wireless or wired communications such as cellular and wireless and can utilize a variety of communication standards such as GSM, GPRS, CDMA, TDMA, Wi-Fi, WiMAX, telephone landline, Ethernet, etc. Processor 320 can include one or multiple data processors that execute software 340 stored in memory 330, utilize and generate data 350 stored in memory 330, and utilize data signals from and to sensors 360.

Memory 330 includes software 340 and data 350. Software 340 includes operating system 342 and applications 344. Operating system 342 manages the operation of processor 320 including interactions with input/output device 310, memory 330 and sensors 360. Applications 344 include a variety of software applications performing specialized functions such as managing user interactions with the mobile device, analyzing those interactions for identifying visual capabilities of the user, comparing those capabilities to baselines, making determinations whether there may be visual impairment, and providing those determinations to the user or to caretakers of the user such as a physician.

Data 350 includes user information 351, baselines 354, alerts 357 and historical data 358. User information 351 can include age 352, general locations 353 where the user typically resides or works, or other information about the user such as health status which may be useful in identifying user visual capabilities. Baselines 354 includes a global baseline 355 downloaded from server 304 and user baseline 356 which has been developed specifically about the user of the mobile device. Global baseline 355 includes information of a large population of users to be used to compare the user to that population. This global baseline information can include average visual interaction patterns of a large group of users with their mobile devices including expected values for healthy individuals and expected values for individuals with various types of visual impairment. These baseline patterns can be stored as visual interaction factors indicating visual health or visual impairment. User baseline 356 includes information regarding visual interaction patterns of the user with the mobile device stored as visual interaction factors including averages, measures of dispersion, outliers, and other statistical information. User baseline 356 may be established early in the user's interactions with the mobile device and may be periodically updated using historical information, although the original baseline may be preserved for analytical purposes such as to identify visual impairment. User baseline may also include information from other mobile devices utilized by the user. Alerts 357 includes alerts or other notifications generated by the mobile device based on identified variances in expected user interaction with the mobile device. For example, if the user consistently starts zooming displayed information indicating issues with viewing smaller type, then an alert or other notification may be generated. This alert or other notification may be shared with the user or shared with a caretaker of the user such as a physician. Historical data 358 includes historical information derived from user interactions with the mobile device. This information can be used to generate or update the user baseline or to identify visual impairment.

Sensors 360 can include a variety of sensors including accelerometer 361, infrared proximity sensor 362, ambient light sensor 363, camera 364, touchscreen 365, microphone 366, timer 367 and other types of sensors which could be useful in determine the user's visual interaction with the mobile device. For example, accelerometer 361 can provide the movement and orientation of the mobile device. In conjunction with an infrared proximity sensor 362, the processor can determine how the user is orienting the mobile device relative to him or herself. Ambient light sensor 363 can provide information regarding ambient light conditions to determine whether the user is viewing the mobile device in low light conditions. In conjunction with camera 364, the face and eyes of the user can be identified to determine how the user is orienting the mobile device as well as to determine where the user is looking when viewing the mobile device. Touchscreen 365 provides information about the user modifying presented content such as displayed images to enlarge type or pan across those images. Microphone 366 can be utilized to determine whether the user is utilizing the software to read out loud a displayed text or for providing vocal commands rather than typed commands. Timer 367 can be utilized to determine whether the user takes longer to read a certain amount of text, how quickly the user zooms text or images, etc. Many other types of sensors can be utilized to determine how the user visually interacts with the mobile device.

Server 304 may be one or more servers communicating information to and from mobile device 302. Server 304 can include input/output devices, processors, memory and other generally known elements that are not shown. Server 304 can include global historical data 380 from a large population of users for statistical use. The identity of individuals may be disguised, such as by using aliases and encryption, so that those individuals cannot be identified without the user's permission. Also included is a global baseline 382 derived from the historical data and other sources to provide a baseline of healthy individuals as well as individuals with specific visual impairments. Management software 384 is also included for managing these processes at the server level and to provide statistical analysis of the historical information to assist in generating and maintaining global baseline 382. Many other types of mobile device and server configurations may be utilized for implementing various embodiments of the invention.

Figure 4:
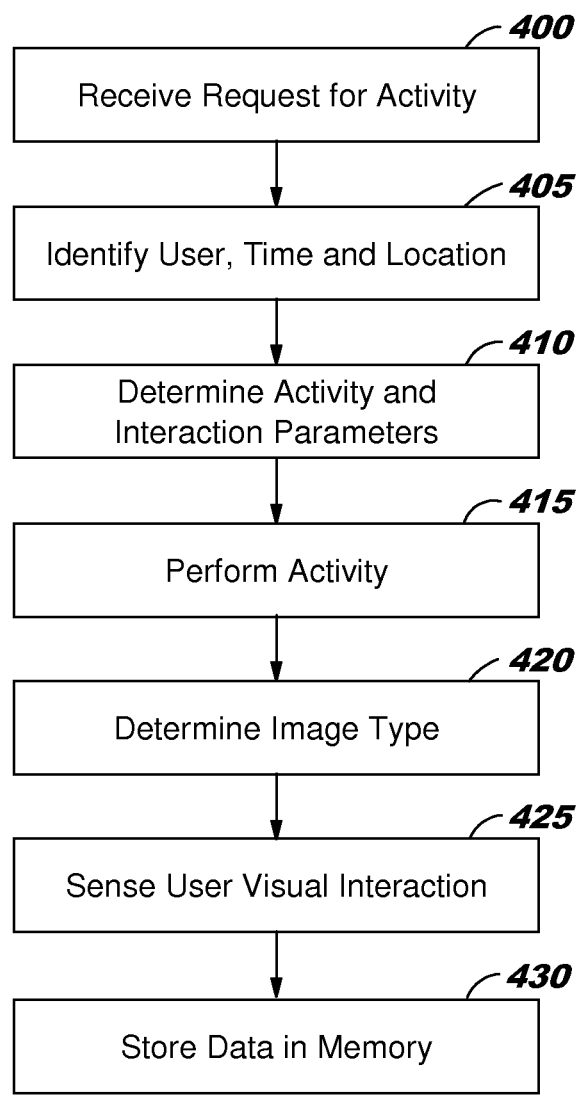
FIG. 4 is a flow diagram of the operation of the mobile device in which various embodiments may be implemented.

FIG. 4 is a flow diagram of the operation of the mobile device in which various embodiments may be implemented. The mobile device may be a mobile phone, tablet, or any one of the mobile devices described above or other mobile devices not shown. In a first step 400, the mobile device receives a request from a user to initiate or perform a normal use activity. This can be a single button pressed by the user to perform an activity such as a button to display a set of applications to select, or it may be a keypad or voice entry of a variety of information such as a request to start an application, display a webpage, display a keyboard for user entry for making a phone call, etc. Normal use activities are activities that are normally performed or utilized by a user and which are for purposes other than testing so that the user is not focused or possibly even aware of being tested. Normal use of a mobile device is when normal use activities are performed or utilized by the user with the mobile device. Such normal use activities on a mobile device include a phone, an email, an internet browser, a map, a camera, a video game, a music player, and a mobile device application selected by the user.

In a second step 405 the user providing the request is identified and the time and location of the mobile device are determined. The user may be identified by the mobile device such as through fingerprint identification, keypad entry of a userid or password, voice recognition with a microphone, facial recognition with a camera, etc. The time can include the time of day as well as the date. The location can be a GPS coordinate or an associated location such as home or office. If there is a single user of the device, then the user identification portion of this step may be skipped. Subsequently in step 410, the mobile device determines the parameters for the desired activity. For example, if the user selects an application to be run, then the activity parameters for running that application are obtained from memory (e.g., obtain current location for finding local restaurants) as well as predetermined interaction parameters based on visual interaction factors for that application or for the mobile device generally are obtained from memory (e.g., distance mobile device display held from users eyes and font size). Alternatively, the user may be queried for the activity parameters (e.g., a phone number to be called, a type of restaurant to search for, etc.). The interaction parameters may be generic default parameters, may automatically vary based on the age or other attributes of the user, and may vary based on input from the user or a user's caretaker or health care provider. The predetermined interaction parameters may be selected to identify specific visual diseases or to help detect general visual degradation.

Once the activity parameters and interaction parameters are obtained, then in step 415 the requested activity is performed in accordance with the parameters. As the requested activity is performed, the type of content being presented (e.g., image being displayed) is determined in step 420. For example, the type of image may be text of a certain font size, a map with extensive horizontal, vertical or diagonal lines, a video such as a movie, a video game, etc. Each type of content presented can provide different visual challenges for a user. For some activities, only a single type of image may be displayed. In case an image type or other presented content cannot be determined, then a copy of the image or set of images may be stored in memory with a time reference, particularly if the user interaction is unusual or outside normal behavior with that image or other content presented.

As the requested activity is performed, in step 425 the mobile device sensors identify the user's visual interaction with the mobile device in accordance with the predetermined interaction parameters based on visual interaction factors. Examples of visual interaction with the mobile device based on visual interaction factors include the requested font size, positioning of the mobile device display, requested image changes, eye distance to the mobile device display, requested image zoom, requested image shrink, eye alignment, eye tracking, user repositioning of the mobile device display, display brightness, ambient brightness, mistyped letters on a displayed keyboard, increased use of voice commands, and time taken to read text, etc.

Finally, in step 430, the identified user, the time and duration of the requested activity, the requested activity and activity parameters, the type of content presented, the predetermined interaction parameters, and the user's visual interaction with the mobile device are stored in historical data for statistical analysis. Other types of parameters, events or other data may be tracked including whether the requested activity was abandoned before completion, task complexity, etc. This information may be stored in memory of the mobile device or stored remotely at a central unit. Such a central unit may be a computer located in the facility or a server or storage unit located remotely across the internet.

FIG. 5 is a flow diagram of analyzing visual interaction with the mobile device for operating patterns indicating visual impairment in accordance with a first embodiment. A user baseline is established for the mobile device, which is then compared to recent operating patterns to determine whether a change has occurred indicating visual impairment. The foregoing assumes a single user, but may easily be modified for several users of the same mobile device as described below. The foregoing may be performed by a central processing unit with activity information from one or more mobile devices (e.g., mobile phone and tablet). Alternatively, the foregoing may be performed individually by the mobile devices with the results forwarded to a processor.

In a first step 500 a counting variable m is set to 0. This variable is utilized to count through the number of mobile devices n being tracked for operating pattern changes. For example, if the operating patterns of three different mobile devices are being tracked for a given user, then n will be equal to 3 and there will be three entries in a database for that user as shown in FIG. 7 below. In a second step 505, counting variable m is incremented by 1. In a third step 506, it is determined whether M is greater than n. If yes, then processing continues to step 550, otherwise processing continues to step 510.

In step 510, it is determined whether a previous baseline was established for mobile device m and whether that baseline is acceptable for current use. The baseline pattern is a statistical pattern established by the user for a given period of time or number of uses of the mobile device. For example, the pattern may be established over 2 weeks or the first 200 uses of the mobile device by the user. The amount of time or number of uses utilized to establish a baseline pattern may differ based on the type of mobile device. The baseline pattern may be recomputed periodically to include more time or uses the longer the period of tracking increases. That is, a baseline may have been previously established but may need a periodic update. If yes in step 510, the current baseline is acceptable, then processing continues to step 530 below otherwise processing continues to step 515.

In step 515, a baseline operating pattern is established for mobile device m. For example, if m is equal to 1 and the first mobile is a mobile phone, then a baseline pattern is established for the mobile phone. In the case of a mobile phone, the pattern can include the type of activity selected, the type of image or other content viewed, the distance the uses holds the mobile phone from the user's eyes, the font size selected, the orientation of the mobile phone (picture or landscape), the angle of viewing, whether the user rocks or adjusts the viewing angle frequently, etc. This pattern can include an average and a standard deviation or other measure of dispersion. This baseline may also be expressed as a similarity or difference from average patterns for a population of users. For example, the user may more frequently angle the display for viewing than the average user. This allows anyone reviewing the resulting data below to better understand the operating patterns of the user within a greater context. Once a baseline is established, that baseline is stored in memory in step 520 for present or future use.

The user interactions utilized to generate the baseline (as well as comparisons against that baseline) may be general or very specific and can be based on the predetermined interaction parameters. The baseline may be based on generic default parameters, may automatically vary based on the age or other attributes of the user, and may vary based on input from the user or a user's caretaker or health care provider. The baseline may be directed to help identify specific visual diseases or to help detect general visual degradation. Vision issues can cause a variety of different symptoms. For example, an increased time spent reading text, more font adjustments, and more zooming may be associated with increased difficulty in reading that text. Increased rocking and positioning of the mobile device may indicate macular degeneration (where portions of the field of vision have degraded so that other portions of the field of vision are utilized by the user to view text or other content). Poor pupil aim and changes thereof over time, particularly of similar images over time (e.g., a weather map of the local area) may indicate retina damage. The distance a mobile device is held from the user's eyes can also indicate visual issues, especially if that distance changes over time. The increased use of voice commands can also indicate general visual degradation. However, if these occur while the user is traveling (e.g., driving a vehicle) as indicated by the GPS signal, then such increased use may be disregarded.

Subsequently in step 530, a short term recent operating pattern and a long term recent operating pattern are generated from the historical data. The short term recent operating pattern includes fewer uses of an mobile device over a shorter period of time (e.g., 48 hours) and is utilized to detect acute recent visual impairment whereas the long term recent operating pattern includes more uses of an mobile device over a longer period of time (e.g., one month) and is utilized to detect chronic or degenerative visual impairment. The short term and long term recent operating patterns are determined similar to the baseline operating pattern to provide consistent pattern types suitable for statistical analysis.

Processing then continues to step 535 where the baseline operating pattern is compared to the short term recent operating pattern and the long term recent operating pattern to look for a set of significant negative pattern differences. That is, positive pattern differences may be ignored in some circumstances. For example, if the user mistypes phone numbers much less often or types phone numbers much more quickly than normal, then those pattern differences may be ignored. Various types of parameters, events or other trackable data may be compared including activity completion time, a required data entry, a complexity of an activity (e.g., reading an email), etc. In step 540, it is determined whether this set of negative pattern differences are statistically significant or otherwise exceeded a predetermined threshold. For example, a health care provider or other responsible party can set a threshold of a statistical confidence percentage (e.g., 95% confident), a statistical variation to be exceeded (e.g., 4 sigma), a simple absolute threshold (e.g., zooms text >50% of the time), or other predetermined threshold. The threshold may be preset for each mobile device or for each user across all mobile devices. The threshold may vary depending on the user's age or other factors. For example, some visual degradation may be expected over time for an 80 year old person but not for a 25 year old person. If not significant, then processing returns to step 505 above, otherwise processing continues to step 545 where the set of pattern differences are stored and flagged for processing as described below and processing returns to step 505 above.

Step 550 is performed after all the mobile devices have been reviewed individually for a set of significant pattern differences (i.e. yes in step 506). In step 550, certain multi-mobile devices comparisons are performed. For example, a mobile phone may be utilized for certain activities such as reading emails during the day and a tablet utilized for watching movies in the evening. Changes to this pattern may indicate a loss of visual acuity (e.g., using the tablet with a larger display to read emails during the day) and resulting visual impairment. Subsequently in step 555 it is determined whether there were any significant multi-mobile device operating pattern observed or if any of the devices have flagged significant negative short term or long term pattern differences. If not, then processing ends for this user, otherwise processing continues to step 560.

In step 560, the set of significant pattern differences are summarized and provided to a predesignated person or persons. This could be in the form of an alert, an email, a text message, a report, or other notification sent to a health care professional, a caregiver or a family member. For example, this could be in a text or email to a mobile phone of a family member, to a server of a responsible physician, etc. The communication may be in summary form only or may include the details of the set of pattern differences. The person receiving the communication can also later download the stored and flagged pattern differences as well as other detailed information to perform additional analysis. The fact that significant pattern differences may have occurred is not diagnostic in and of itself, but is a tool to allow others such as medical professionals to utilize the information in performing further testing and diagnostic analysis of possible visual impairment, whether acute or longer term. Processing then ceases for this user, although the above described process is repeated for each user of the mobile devices.

Each type of mobile devices can have a different set of activities, activity parameters, interaction patterns, sensing capabilities, and operating patterns which can be captured and utilized to identify possible visual impairment. With smart mobile devices, these elements may be updated periodically by the manufacturer, seller or maintenance entity for each mobile device. Furthermore, additional pattern recognition capabilities may be introduced based on recommendations of a health care professional or as research better identifies interaction parameters based on visual interaction factors useful for detecting visual impairment.

Many types of parameters, events, sensor results, and user modifications can be identified and captured for pattern analysis. This information may be collected by the mobile devices directly or through other sensors within or outside a facility. Some examples of information gathering by mobile devices are provided above. One of ordinary skill may generate many other possible patterns to observe utilizing these and other mobile devices.

FIG. 6 is a flow diagram of analyzing visual interaction with the mobile device for operating patterns indicating visual impairment in accordance with a second embodiment. A user baseline is established for the mobile device, which is then compared to recent operating patterns to determine whether a change has occurred indicating visual impairment. The foregoing assumes a single user, but may easily be modified for several users of the same mobile device as described below. The foregoing may be performed by a central processing unit with activity information from one or more mobile devices (e.g., mobile phone and tablet). Alternatively, the foregoing may be performed individually by the mobile devices with the results forwarded to a processor.

In a first step 600 a counting variable m is set to 0. This variable is utilized to count through the number of mobile device n being tracked for operating pattern changes. For example, if the operating patterns of three different mobile devices are being tracked for a given user, then n will be equal to 3 and there will be three entries in a database for that user as shown in FIG. 7 below. In a second step 605, counting variable m is incremented by 1. In a third step 606, it is determined whether M is greater than n. If yes, then processing continues to step 660, otherwise processing continues to step 610.

In step 610, a baseline operating pattern is established for mobile device m. For example, if m is equal to 1 and the first mobile is a mobile phone, then a baseline pattern is established for the mobile phone. In the case of a mobile phone, the pattern can include the type of activity selected, the type of image or other content viewed, the distance the uses holds the mobile phone from the user's eyes, the font size selected, the orientation of the mobile phone (picture or landscape), the angle of viewing, whether the user rocks or adjusts the viewing angle frequently, etc. This pattern can include an average and a standard deviation or other measure of dispersion. This baseline may also be expressed as a similarity or difference from average patterns for a population of users. For example, the user may more frequently angle the display for viewing than the average user. This allows anyone reviewing the resulting data below to better understand the operating patterns of the user within a greater context. Once a baseline is established, that baseline is stored in memory in step 615 for present or future use. In alternative embodiments, the baseline may be stored in memory for future use, although the focus of this embodiment is to generate a new baseline each time this process is executed. This is to have as complete a history as practical incorporated into the baseline for more accurate detection capabilities.

Subsequently in step 620, a short term recent operating pattern is established. The short term recent operating pattern includes recent uses of a mobile device over a short period of time (e.g., 48 hours) and is primarily utilized to detect acute recent visual impairment whereas a long term recent operating pattern includes more uses of a mobile device over a longer period of time (e.g., one month) and is utilized to detect chronic or degenerative visual impairment. The short term operating pattern is determined similar to the baseline operating pattern to provide consistent pattern types suitable for statistical analysis.

Processing then continues to step 625 where the baseline operating pattern is compared to the short term recent operating pattern to identify a set of significant negative pattern differences. That is, positive pattern differences may be ignored in some circumstances. For example, if the user mistypes phone numbers much less often or types phone numbers much more quickly than normal, then those pattern differences may be ignored. Various types of parameters, events or other trackable data may be compared including activity completion time, a required data entry, a complexity of an activity (e.g., reading an email), etc. In step 630, it is determined whether these negative pattern differences are statistically significant or otherwise exceeded a predetermined threshold. For example, a health care provider or other responsible party can set a threshold of a statistical confidence percentage (e.g., 95% confident), a statistical variation to be exceeded (e.g., 5 sigma), a simple absolute threshold (e.g., zooms text >50% of the time), or other predetermined threshold. The threshold may be preset for each mobile device or for each user across all mobile devices. The threshold may vary depending on the user's age or other factors. For example, some visual degradation may be expected over time for an 80 year old person but not for a 25 year old person. If not significant, then processing proceeds to step 640 below. Otherwise processing continues to step 635 where the set of pattern differences are stored and flagged for processing as described below and processing then continues to step 640 below.

In step 640, recent long term operating patterns are derived from the baseline to identify whether any of the recent operating patterns indicate a negative change in user performance. For example, operating patterns for the past 30, 60, 90, 180, 270 and 360 days may be derived from the long term baseline to determine whether there may be possible long term visual degradation. Alternatively, these recent long term operating patterns may be independently generated from the underlying historical data. The various long term operating patterns are then compared to the overall baseline trends in step 645 to identify possibly long term visual degradation. For example, the user may have shown a slow normal decline which then turns significantly worse for one or more of the recent long term operating patterns. For multiyear pattern analysis, this embodiment helps prevent false positives which may be caused by normal visual degradation. This embodiment also includes all or nearly all historical data in the baseline for statistical analysis. Various types of parameters, events or other trackable data may be compared including activity completion time, a required data entry, a complexity of an activity (e.g., reading an email), etc. In step 650, it is determined whether these negative pattern differences are statistically significant or otherwise exceeded a predetermined threshold. For example, a health care provider or other responsible party can set a threshold of a statistical confidence percentage (e.g., 95% confident), a statistical variation to be exceeded (e.g., 5 sigma), a simple absolute threshold (e.g., zooms text >50% of the time), or other predetermined threshold. The threshold may be preset for each mobile device or for each user across all mobile devices. If not significant, then processing returns to step 605 above. Otherwise processing continues to step 655 where the set of pattern differences are stored and flagged for processing as described below and processing continues to step 605 above.

Step 660 is performed after all the mobile devices have been reviewed for significant pattern differences (i.e. yes in step 606). In step 660 certain multi-mobile device comparisons are performed. For example, a mobile phone may be utilized for certain activities such as reading emails during the day and a tablet utilized for watching movies in the evening. Changes to this pattern may indicate a loss of visual acuity (e.g., using the tablet with a larger display to read emails during the day) and resulting visual impairment. Subsequently in step 665, it is determined whether any of the mobile devices have flagged significant negative short term or long term pattern differences. If not, then processing ends for this user, otherwise processing continues to step 670. In step 670, the set of significant pattern differences are summarized and provided to a predesignated person or persons. This could be in the form of an alert, an email, a text message, a report, or other notification sent to a health care professional, a caregiver or a family member. For example, this could be in a text or email to a mobile phone of a family member, to a server of a responsible physician, etc. The communication may be in summary form only or may include the details of the pattern differences. The person receiving the communication can also later download the stored and flagged pattern differences as well as other detailed information to perform additional analysis. The fact that set of significant pattern differences may have occurred is not diagnostic in and of itself, but is a tool to allow others such as medical professionals to utilize the information in performing further testing and diagnostic analysis of possible visual impairment, whether acute or longer term. Processing then ceases for this user, although the above described process can be repeated for each user of the mobile devices.

Each type of mobile device can have a different set of activities, activity parameters, sensing capabilities, interaction parameters, and operating patterns which can be captured and utilized to identify possible visual impairment. With smart mobile devices, these elements may be updated periodically by the manufacturer, seller or maintenance entity for each mobile device. Furthermore, additional pattern recognition capabilities may be introduced based on recommendations of a health care professional or as research better identifies parameters useful for detecting visual impairment. Examples of such types of activities for given mobile devices are described above.

Although the above two embodiments describe statistical analysis on a mobile device by mobile device basis, alternative embodiments may utilize statistical analysis across multiple mobile devices. For example, zooming text consistently may be analyzed across multiple mobile devices such as a mobile phone, PDA, tablet, laptop, etc.

In an alternative embodiment, occasional modifications to the presented content (e.g., displayed image) may be utilized to test certain user interactions. These modifications to the presented content may be subliminal or sufficiently non-distracting to not interfere with the normal use of the mobile device. For example, a section of displayed text may be quickly flashed or icons temporarily inserted in the presented content. If the user glances over at the flashed text or inserted icon, then that text or icon was in the user's field of vision. If the user consistently does not look at flashed text or inserted icons from a certain area in their field of vision, but does so in other areas in the field of vision, then the user may have some loss of vision. These occasional modifications may only be utilized when certain visual impairments are indicated or upon the instruction of a health care provider.

FIGS. 7A-7B are block diagrams of data structures utilized for storing visual interaction with the mobile device for statistical analysis in which various embodiments may be implemented. FIG. 7A is directed to a data structure 700 listing mobile devices and their various capabilities. There are columns for each mobile device number or ID 705, mobile device activity 710, activity parameter ranges 715, sensor capabilities 720, possible events 725, and threshold 730. This data structure includes at least one entry for each mobile device and standard mobile device activity. For example, if a mobile device has twenty standard activities (e.g., email, text, phone, weather, internet, movies, etc.), then there would be twenty entries in data structure 700 for that mobile device. Each activity has parameter ranges such as font utilized, whether shown in portrait or landscape format, etc. There are various sensor capabilities such as an image sensor which can determine whether text is being displayed, a connection to the display touch sensor to determine when the user is zooming an image or other presented content, and a camera for determining the distance that the user's eyes are from the mobile device. A threshold for determining significance is also provided, which is a 95% confidence of a statistically significant event in this example. In this example, the predetermined threshold is preset by mobile device. Alternatively, the threshold may be predetermined by user. Alternative embodiments could utilize many alternative data structures and values to capture the same information in a readily accessible and usable layout.

FIG. 7B is directed to a historical database 750 for maintaining a listing of activities by the user(s) for a variety of mobile devices. There are columns for user ID 755, activity time 760 (including date and time), mobile device number or ID 765, requested activity 770, activity and interaction parameters 775, sensor results 780, and interaction events detected 785. This data structure includes one entry for each mobile device operation by a user. For example, if a user utilizes the mobile phone and ends up incorrectly entering the pass code twice, then that information is captured for future analysis.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A data processing system suitable for storing and/or executing program code will include at least one processor coupled directly or indirectly to memory elements through a system bus. The memory elements can include local memory employed during actual execution of the program code, bulk storage media, and cache memories, which provide temporary storage of at least some program code in order to reduce the number of times code must be retrieved from bulk storage media during execution.

A data processing system may act as a server data processing system or a client data processing system. Server and client data processing systems may include data storage media that are computer usable, such as being computer readable. A data storage medium associated with a server data processing system may contain computer usable code such as for detecting visual impairment through normal use of a mobile device. A client data processing system may download that computer usable code, such as for storing on a data storage medium associated with the client data processing system, or for using in the client data processing system. The server data processing system may similarly upload computer usable code from the client data processing system such as a content source. The computer usable code resulting from a computer usable program product embodiment of the illustrative embodiments may be uploaded or downloaded using server and client data processing systems in this manner.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to explain the principles of the invention, the practical application, and to enable others of ordinary skill in the art to understand the invention for various embodiments with various modifications as are suited to the particular use contemplated.

The terminology used herein is for the purpose of describing particular embodiments and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of detecting visual interaction factors indicative of visual impairment of a user through normal use of a mobile device comprising:
   responsive to the user requesting utilization of an application on the mobile device, obtaining predetermined visual interaction parameters for the application from a device memory;
   monitoring and recording in the device memory visual interaction of the user with content presented by the mobile device during normal use of the requested application on the mobile device in accordance with the predetermined parameters;
   establishing a baseline pattern of visual interaction factors in accordance with the predetermined parameters;
   utilizing a processor to compare the visual interaction of the user with the baseline factors to determine a set of differences; and
   responsive to the set of differences exceeding a predetermined threshold, providing a notification of visual impairment;
   wherein the requested application is requested by the user for normal use primarily for purposes other than testing.

2. The method of claim 1 wherein the predetermined parameters are established based on known indicators of visual diseases.

3. The method of claim 2 wherein the predetermined parameters and predetermined thresholds are provided by a health care professional.

4. The method of claim 3 wherein the predetermined thresholds are statistically significant differences between the visual interaction of the user with the baseline factors.

5. The method of claim 1 further comprising presenting icons periodically as an element of the content presented by the mobile device; wherein visual interaction of the user includes visual interaction of the user with the presented icons.

6. The method of claim 1 further comprising:
   responsive to the user requesting utilization of a second application on a second mobile device, obtaining second predetermined visual interaction parameters for the second application;
   monitoring and recording visual interaction of the user with content presented by the second mobile device during normal use of the second requested application on the second mobile device in accordance with the second predetermined parameters;
   establishing a second baseline pattern of visual interaction factors in accordance with the second predetermined parameters;
   comparing visual interaction of the user with the second baseline factors to determine a second set of differences; and
   responsive to both sets of differences exceeding a set of predetermined thresholds, providing a combined notification of visual impairment.

7. The method of claim 1 wherein visual interaction factors are selected from a group consisting of requested font size, positioning of the mobile device display, requested image changes, eye distance to the mobile device display, requested image zoom, requested image shrink, eye alignment, eye tracking, user repositioning of the mobile device display, display brightness, ambient brightness, mistyped letters on a displayed keyboard, increased use of voice commands, and time taken to read text.

8. The method of claim 4 further comprising presenting icons periodically as an element of the content presented by the mobile device; wherein visual interaction of the user includes visual interaction of the user with the presented icons; wherein normal use of the mobile devices includes content provided by at least one of a phone, an email, an internet browser, a map, a camera, a video game, a music player, and a mobile device application selected by the user; and wherein visual interaction factors are selected from a group consisting of requested font size, positioning of the mobile device display, requested image changes; eye distance to the mobile device display, requested image zoom, requested image shrink, eye alignment, eye tracking, user repositioning of the mobile device display, display brightness, ambient brightness, mistyped letters on a displayed keyboard, increased use of voice commands, and time taken to read text.

9. A computer program product for detecting visual interaction factors indicative of visual impairment of a user through normal use of a mobile device, the computer program product comprising a computer readable storage medium having program instructions embodied therewith, the program instructions executable by a processing circuit to cause the device to perform a method comprising:
responsive to the user requesting utilization of an application on the mobile device, obtaining predetermined visual interaction parameters for the application from a device memory;
monitoring and recording in the device memory visual interaction of the user with content presented by the mobile device during normal use of the requested application on the mobile device in accordance with the predetermined parameters;
establishing a baseline pattern of visual interaction factors in accordance with the predetermined parameters;
utilizing a processor to compare the visual interaction of the user with the baseline factors to determine a set of differences; and
responsive to the set of differences exceeding a predetermined threshold, providing a notification of visual impairment;
wherein the requested application is requested by the user for normal use primarily for purposes other than testing.

10. The computer program product of claim 9 wherein the predetermined parameters are established based on known indicators of visual diseases.

11. The computer program product of claim 10 wherein the predetermined parameters and predetermined thresholds are provided by a health care professional.

12. The computer program product of claim 11 wherein the predetermined thresholds are statistically significant differences between the visual interaction of the user with the baseline factors.

13. The computer program product of claim 9 further comprising presenting icons periodically as an element of the content presented by the mobile device; wherein visual interaction of the user includes visual interaction of the user with the presented icons.

14. The method of claim 9 further comprising:
responsive to the user requesting utilization of a second application on a second mobile device, obtaining second predetermined visual interaction parameters for the second application;
monitoring and recording visual interaction of the user with content presented by the second mobile device during normal use of the second requested application on the second mobile device in accordance with the second predetermined parameters;
establishing a second baseline pattern of visual interaction factors in accordance with the second predetermined parameters;
comparing visual interaction of the user with the second baseline factors to determine a second set of differences; and
responsive to both sets of differences exceeding a set of predetermined thresholds, providing a combined notification of visual impairment.

15. A data processing system for detecting visual interaction factors indicative of visual impairment of a user through normal use of a mobile device, the data processing system comprising:
a processor; and
a device memory storing program instructions which when executed by the processor execute the steps of:
responsive to the user requesting utilization of an application on the mobile device, obtaining predetermined visual interaction parameters for the application from the computer memory;
monitoring and recording in the device memory visual interaction of the user with content presented by the mobile device during normal use of the requested application on the mobile device in accordance with the predetermined parameters;
establishing a baseline pattern of visual interaction factors in accordance with the predetermined parameters;
utilizing the processor to compare the visual interaction of the user with the baseline factors to determine a set of differences; and
responsive to the set of differences exceeding a predetermined threshold, providing a notification of visual impairment;
wherein the requested application is requested by the user for normal use primarily for purposes other than testing.

16. The data processing system of claim 15 wherein the predetermined parameters are established based on known indicators of visual diseases.

17. The data processing system of claim 16 wherein the predetermined parameters and predetermined thresholds are provided by a health care professional.

18. The data processing system of claim 17 wherein the predetermined thresholds are statistically significant differences between the visual interaction of the user with the baseline factors.

19. The data processing system of claim 15 further comprising presenting icons periodically as an element of the content presented by the mobile device; wherein visual interaction of the user includes visual interaction of the user with the presented icons.

20. The data processing system of claim 15 further comprising:
responsive to the user requesting utilization of a second application on a second mobile device, obtaining second predetermined visual interaction parameters for the second application;
monitoring and recording visual interaction of the user with content presented by the second mobile device during normal use of the second requested application on the second mobile device in accordance with the second predetermined parameters;
establishing a second baseline pattern of visual interaction factors in accordance with the second predetermined parameters;
comparing visual interaction of the user with the second baseline factors to determine a second set of differences; and
responsive to both sets of differences exceeding a set of predetermined thresholds, providing a combined notification of visual impairment.

* * * * *